US008133479B2

(12) United States Patent
Ito (10) Patent No.: US 8,133,479 B2
(45) Date of Patent: Mar. 13, 2012

(54) HAIR RESTORER

(75) Inventor: Yoshiyasu Ito, Tokyo (JP)

(73) Assignee: Cosmo Oil Co., Ltd., Minato-Ku, Tokyo (JP)

( * ) Notice: Subject to any disclaimer, the term of this patent is extended or adjusted under 35 U.S.C. 154(b) by 39 days.

(21) Appl. No.: 11/568,322

(22) PCT Filed: Jul. 6, 2004

(86) PCT No.: PCT/JP2004/009894
§ 371 (c)(1),
(2), (4) Date: Jul. 5, 2007

(87) PCT Pub. No.: WO2005/105022
PCT Pub. Date: Nov. 10, 2005

(65) Prior Publication Data
US 2007/0249721 A1 Oct. 25, 2007

(30) Foreign Application Priority Data

Apr. 28, 2004 (JP) .................................. 2004-134709

(51) Int. Cl.
*A61Q 5/00* (2006.01)
(52) U.S. Cl. ...................... 424/70.1; 424/600; 424/646
(58) Field of Classification Search .................... None
See application file for complete search history.

(56) References Cited

U.S. PATENT DOCUMENTS

| 5,470,876 | A | * | 11/1995 | Proctor | 514/492 |
| 6,136,860 | A | * | 10/2000 | Rushton | 514/561 |
| 6,194,440 | B1 | * | 2/2001 | Steiner et al. | 514/340 |
| 6,376,557 | B1 | * | 4/2002 | Zaveri | 424/725 |
| 6,435,193 | B1 | * | 8/2002 | Cannell et al. | 132/203 |
| 6,638,528 | B1 | * | 10/2003 | Kanios | 424/449 |
| 7,220,779 | B2 | * | 5/2007 | Oshida et al. | 514/563 |
| 2002/0146439 | A1 | * | 10/2002 | DeLong et al. | 424/401 |
| 2003/0212127 | A1 | | 11/2003 | Glassman et al. | 514/458 |
| 2006/0265028 | A1 | * | 11/2006 | Houle et al. | 607/88 |

FOREIGN PATENT DOCUMENTS

| CA | 2455539 A1 | 1/2004 |
| GB | 2106386 | 4/1983 |
| GB | 2314019 | 12/1997 |
| JP | 2-108612 A | 4/1990 |
| JP | 8-337515 A | 12/1996 |
| JP | 08-337563 | 12/1996 |
| JP | 11-116446 | * 4/1999 |
| JP | 11-116446 A | 4/1999 |
| JP | 11-171852 | 6/1999 |
| JP | 2003-095878 A | 4/2003 |
| WO | 96/28412 | 9/1996 |
| WO | 01/85125 | 11/2001 |
| WO | WO 03/011275 | 2/2003 |

OTHER PUBLICATIONS

Wikipedia Dictionary "transdermal".*
International Search Report for International Application No. PCT/JP2004/009894, mailed Oct. 19, 2004 and English translation thereof.
Supplementary European Search Report which was cited in a corresponding Foreign counterpart application (EP 04747362) with the date of completion of the search as Mar. 31, 2009.
English Abstract of JP 08-337563.
Communication dated Oct. 25, 2011 received in the counterpart foreign application No. 04 747 362.4.

* cited by examiner

*Primary Examiner* — Jyothsna Venkat
(74) *Attorney, Agent, or Firm* — Locke Lord LLP (57) ABSTRACT

The object of the present invention is to provide a hair restorer which exhibits a stimulatory effect on hair restoration against hair loss, hair thinning, split ends, hair graying, etc., with higher stability and safety than those of known hair restorers containing 5-aminolevulinic acids as active components. By using 5-aminolevulinic acid or its salt or its derivative, and a composition containing iron sodium diethylenetriaminepentaacetate or iron ammonium diethylenetriaminepentaacetate as active components, a hair restorer and a method for restoring hair which are excellent in hair growth promotion, and stability and safety, are provided.

2 Claims, 4 Drawing Sheets

HAIR RESTORER

CROSS REFERENCE TO RELATED APPLICATIONS

This application is a national phase application under 35 U.S.C. §371 of International Application No. PCT/JP2004/009894 filed Jul. 6, 2004, which claims priority under 35 U.S.C. §119 (a)-(d) to Japanese patent application number JP2004-134709, filed Apr. 28, 2004, the entire contents of which all are hereby incorporated by reference.

TECHNICAL FIELD

The present invention relates to a hair restorer having pilatory effects such as excellent prevention of hair loss and hair growth effect, which is utilized in the fields of pharmaceuticals, quasi-drugs, or cosmetics, and in particular, to the improvement of a hair restorer having 5-aminolevulinic acids as active components, and to a hair restorer wherein 5-aminolevulinic acids and an iron compound are used in combination.

BACKGROUND ART

Conventionally, hair cosmetics focused on the prevention and the amelioration of alopecia have been developed. Since male pattern alopecia cases make up high percentage of all alopecia cases, the application of components having an antiandrogenic action has been particularly examined, and those which competitively inhibit the binding of dihydrotestosterone, which is an activated testosterone, to receptors, and those which inhibit testosterone 5 α-reductase, which is an enzyme that catalyzes the conversion of testosterone into dihydrotestosterone, have been disclosed. An example of the former includes cyproterone acetate, and examples of the latter include androstanone derivatives, bicycloheptenone derivatives, phenoxybutane derivatives, tocopherylquinone, tropolone derivatives, ubiquinone, and also, extracts from many plants including labiatae and asteraceae (for example, see Japanese Laid-open Patent Application Nos. 5-339133 and 7-330555, and Tokushima Journal of Experimental Medicine, 9, 37-59 (1962)), and extracts from mushrooms (for example, see Japanese Laid-open Patent Application No. 11-193220).

In addition, the application of the followings has been examined: those which have a stimulatory effect on the circulation in the scalp, such as 6-(1-piperidinyl)-2,4-pyrimidinediamine-3-oxide (minoxidil) (for example, see the specification of U.S. Pat. No. 4,139,619), cepharanthin, vitamin E derivatives, carpronium chloride, and urea (for example, see Japanese Laid-open Patent Application No. 7-267830); and those which have an activating effect on hair follicles including hair matrix cells, such as adenosine triphosphate, urogastrone, baicalein, pantetheine-S-sulfonate, and odd-chain fatty acid derivatives. Further, external preparations for the head in which 5-aminolevulinic acids, which are already known as herbicides, plant regulators, etc., are contained as active components, are known (for example, see Japanese Laid-open Patent Application No. 11-116446).

However, other than testosterone-dependent male pattern alopecia, alopecia is triggered by various causes such as aging, malnutrition, and stress, which is particularly popular in the modern society. For alopecia other than male pattern alopecia thus described, the effect of components having an antiandrogenic action cannot be expected, and further, among the components having the antiandrogenic action mentioned above, there are many components that might express a side effect, that show poor stability in a cosmetic base, or that show an insufficient action effect. In addition, as to components derived from natural products such as plant extracts, there are many components that are difficult to be obtained with a certain quality, and that have undesirable colors and odors to be blended into cosmetics. Further, among those reported to have a stimulatory effect on the circulation in the scalp and to have an activating effect on hair follicles, there are not many components with which a sufficient action effect can be obtained at a low concentration, and some components have problems in their stability and safety.

Conventionally known external preparations for head (hair restorers) containing 5-aminolevulinic acids as active components cannot be used stably because of the following reasons; they cause damages to hair when they are not used in accordance with the direction of their dosage and use, resulting in problems such as split ends and decrease in the number of hairs, and in addition, light shielding at the point of use is an absolute requirement. The object of the present invention is to solve problems in use of external preparations for the head containing 5-aminolevulinic acids as active components, and to provide a hair restorer with higher stability and safety, whose usage is simple, and which exhibits an excellent stimulatory effect on hair restoration against hair loss, hair thinning, split ends, hair graying, etc.

In order to solve the above-mentioned problems caused by using 5-aminolevulinic acids, the present inventor made a keen study by conducting experiments with a lot of compounds and studied intensively on the assumption that the use of 5-aminolevulinic acid in combination with other various compounds would lead to a simple usage, and the exhibition of safe and stable hair restoring effect. As a result, the present inventor has found that the problems that occurred when 5-aminolevulinic acid was used alone, such as hair removal and light shielding condition at the point of use, can be avoided by using 5-aminolevulinicacids and iron compounds in combination, and the present invention has been thus completed.

DISCLOSURE OF THE INVENTION

The present invention relates to a hair restorer which contains one or more compounds selected from 5-aminolevulinic acid or its salt or a derivative of them, and an iron compound, as active components. The hair restorer may further contain urea as an active component. According to the present invention, the iron compound may be one or more compounds selected from ferrous citrate, iron sodium citrate, iron ammonium citrate, iron acetate, iron oxalate, ferrous succinate, iron sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate. Preferably, the iron compound is iron sodium diethylenetriaminepentaacetate or iron ammonium diethylenetriaminepentaacetate. The present invention also relates to a method for restoring hair by transdermally administering a hair restorer which contains one or more compounds selected from 5-aminolevulinic acid or its salt or a derivative of them, and an iron compound, as active components. The hair restorer in the method for restoring hair may further contain urea as an active component. The iron compound in the method for restoring hair may be one or more compounds selected from ferrous citrate, iron sodium citrate, iron ammonium citrate, iron acetate, iron oxalate, ferrous succinate, iron sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate. Preferably, the iron compound in the method for restoring hair is iron sodium diethylenetriaminepentaacetate or iron ammonium diethylenetriaminepentaacetate.

BEST MODE OF CARRYING OUT THE INVENTION

The hair restorer of the present invention is not particularly limited as long as it contains one or more compounds selected from 5-aminolevulinic acid or its salt or a derivative of them, and an iron compound, as active components. In addition, the method for restoring hair of the present invention is not particularly limited as long as it is a method wherein a hair restorer which contains one or more compounds selected from 5-aminolevulinic acid or its salt or a derivative of them, and an iron compound, as active components is transdermally administered to the head. The above-mentioned 5-aminolevulinic acid is also referred to as δ-aminolevulinic acid, and is one of amino acids and shown by the formula HOOC—$(CH_2)_2$—(CO)—$CH_2$—$NH_2$ (hereinafter, also referred to as 5-ALA). This 5-aminolevulinic acid widely distributes in various organisms, and is generally biosynthesized by 5-aminolevulinic acid synthetase from succinyl CoA and glycine. This 5-aminolevulinic acid is also known as an intermediate of porphyrin biosynthesis.

Examples of salts of 5-aminolevulinic acid of the present invention include acid addition salts such as hydrochloride, phosphate, nitrate, sulfate, acetate, propionate, butylate, valerate, citrate, fumarate, maleate, and malate; and metal salts such as sodium salt, potassium salt, and calcium salt. It is preferable that these salts are used as aqueous solutions, suspensions, or powders, and have a same effect as that of 5-aminolevulinic acid.

As a representative embodiment of 5-aminolevulinic acid derivatives used as active components of the hair restorer of the present invention, 5-aminolevulinic acid ester and N-acyl-5-aminolevulinic acid are exemplified. As an embodiment of 5-aminolevulinic acid ester, for example, the followings are exemplified: optionally substituted linear, branched or cyclic alkyl ester having 1 to 24 carbon atoms, preferably, for example, 5-aminolevulinic acid ester whose ester residue is a methyl group, an ethyl group, an isopropyl group, an n-hexyl group, a cyclohexyl group, an n-heptyl group, an n-octyl group, an n-nonyl group, an n-dodecyl group, an n-hexadecyl group, a benzyl group, a phenethyl group, a 3-phenylpropyl group, a hydroxyethyl group, and an ethoxyethyl group. In addition, as a substituent these alkyl groups can have, for instance, the followings are exemplified: a hydroxyl group, an alkoxy group, a phenyl group, a benzyl group, and a hydroxymethyl group. Further, as N-acyl-5-aminolevulinic acid, a compound wherein an amino group of 5-aminolevulinic acid is acylated with, for example, an alkanoyl group, an aromatic acyl group, a benzyloxycarbonyl group or the like, each having 1 to 24 carbon atoms, is exemplified. Still further, as a preferable embodiment of an N-acyl group, for instance, the followings are specifically exemplified: an acetyl group, an n-pentanoyl group, an n-hexanoyl group, an n-nonanoyl group, a benzoyl group, and a benzyloxycarbonyl group.

These 5-aminolevulinic acid ester and N-acyl-5-aminolevulinic acid can be produced, for example, by publicly known chemical synthesis methods such as methods described in Japanese Laid-open Patent Application No. 4-9360. In addition to the chemical synthesis, they can be produced by production methods either by microorganisms or by enzymes. Further, a roughly-purified product containing an object obtained in the process of the production can be also used without separation and purification as long as the roughly-purified product does not contain a toxic substance. 5-aminolevulinic acid, its salt, and their derivatives can be used alone, or by mixing two or more of them.

The iron compound of the present invention is not particularly limited as long as it is a compound having iron in its molecule. Examples of the iron compound include ferrous citrate, iron sodium citrate, iron ammonium citrate, iron acetate, iron oxalate, ferrous succinate, iron sodium succinate citrate, ferrous pyrophosphate, ferric pyrophosphate, heme iron, iron dextran, iron lactate, ferrous gluconate, iron sodium diethylenetriaminepentaacetate, iron ammomium diethylentriaminepentaacetate, iron sodium ethylenediaminetetraacetate, iron ammonium ethylenediaminetetraacetate, iron triethylenetetraamine, iron sodium dicarboxymethylglutamate, iron ammonium dicarboxymethylglutamate, iron choline citrate, ferrous formate, ferric formate, ferric ammonium potassium oxalate, ferrous sulfate, ferric sulfate, iron ammonium sulfate, ferric carbonate, ferrous chloride, ferric chloride, ferric pyrophosphate, and iron oxide. Among them, iron sodium diethylenetriaminepentaacetate and iron ammomium diethylenetriaminepentaacetate are preferable.

As the hair restorer of the present invention, those further containing urea as an active component are preferable. Urea is a colorless to white crystal or crystalline powder, and is freely soluble in water, soluble in ethanol, and can be formed into many kinds of dosage forms such as lotions and creams, as external preparations. In addition, urea has a high affinity for skin, and therefore, it has a suitable property as a component of hair restorers. Though it depends on a base material and other components used simultaneously, it is possible to blend urea into the hair restorer of the present invention at a ratio of 0.01 to 40 (W/W %; weight ratio), preferably 0.1 to 10%. As urea for use, commercially available urea can be used directly.

In the present invention, components usually used in hair restorers can be blended to the extent that they do not damage the effect of the present invention. Examples of such components include: excipients, vasodilating agents (carpronium chloride, benzyl nicotinate, *Swertia japonica* extract, *Panax schin-seng* Nees extract, vitamin E acetate, pepper tincture, etc.), antihistamines (diphenhydramine hydrochloride, isothipendyl hydrochloride, etc.), anti-inflammatory agents (glycyrrhetinic acid, guaiazulene, etc.), bactericides (chlorhexidine gluconate, isopropylmethylphenol, quarternary ammonium salt, hinokitiol, piroctone olamine, etc.), moisturizing agents (sodium hyaluronate, chondroitin sulfate, etc.), extracts of various animals and plants (*Taxus cuspidata, Moutan Cortex, Glycyrrhiza glabra, Hypericum erectum, Aconitum, Eriobotrya japonica, Artemisia capillaris, Symphytum officinale, Angelica keiskei, Crocus sativus, Gardeniae Fructus, Rosmarinus officinalis, Salvia officinalis, Saussurea costus, Saussurea Root, Humulus lupulus*, placenta, etc.), vitamins (retinal acetate, pyridoxine hydrochloride, ascorbic acid, thiamine nitrate, cyanocobalamin, biotin, etc.), water, lower alcohols (methanol, ethanol, denatured ethanol, isopropyl alcohol, etc.), antioxidants (dibutylhydroxytoluene, sodium pyrosulfite, tocopherol, sodium edetate, ascorbic acid, isopropyl gallate, etc.), auxiliary solubilizers (diisopropyl adipate, isopropyl myristate, polyethylene glycol, medium-chain triglyceride, fatty acid esters, various vegetable oils, various animal oils, polyalcohol fatty acid ester, alkyl glycerine ether, hydrocarbons, lactic acid, sodium hydroxide, etc.), metabolism activating agents (panthenol, etc.), surface active agents (sorbitan fatty acid ester, glycerine fatty acid ester, polyglycerine fatty acid ester, propylene glycol fatty acid ester, polyoxyethylene sorbitan fatty acid ester, polyoxyethylene sorbit fatty acid ester, polyoxyethylene glycerine fatty acid ester, polyethylene glycol fatty acid ester, polyoxyethylene alkyl ether, polyoxyethylene polyoxypropylene alkyl ether, polyoxyethylene alkylphenyl ether, polyoxyethylene hydrogenated castor oil, polyoxyethylene castor oil, polyoxyethylene beeswax derivatives, polyoxyethylene lanolin derivatives, polyoxyethylene alkylamide, polyoxyethylene alkylamine, lecithin derivatives, polymeric emulsifiers, etc.), emulsion stabilizers (higher alcohols, etc.), gelling agents (water-soluble polymers, etc.), adhesives, fragrances, fresheners (menthol, peppermint oil, camphor, etc.), and dyes.

As mentioned above, the hair restorer of the present invention is characterized by containing 5-aminolevulinic acid or its salt or a derivative of them and an iron compound, and as for its dosage form, any of powders, liquids and ointments can be employed. It can be prepared into dosage forms such as lotions, emulsions, creams (ointments), gels, and aerosols, according to methods usually used (for example, methods prescribed in The Japanese Pharmacopoeia $12^{th}$ Edition). It is also possible to apply 5-aminolevulinic acid or its salt or a derivative of them and an iron compound to the same affected area in different dosage forms.

When prepared as aqueous solutions such as lotions, or creams (ointments), in order to prevent the degradation of 5-aminolevulinic acid or its salt or a derivative of them, it is preferable to prepare the hair restorer while paying attention not to cause alkalinization. In case where the alkalinization occurs, the degradation can be prevented by removing oxygen. With attention to this point, it can be used in combination with components of liquids or ointments usually used.

In the method for restoring hair of the present invention, it is preferable that the hair restorer of the present invention mentioned above is transdermally administered to an affected area by methods such as spraying, application, and putting a poultice, however, it can be also transdermally administered to the entire scalp appropriately. In general, when it is applied to the entire scalp of an adult, it is preferable to administer 5-aminolevulinic acid or its salt and derivative, which are active ingredients, in an amount of 10 μg to 10 mg, desirably 100 μg to 5 mg, more desirably 1 mg to 5 mg, in 5-aminolevulinic acid hydrochloride equivalent. The dose of iron compounds to be combined with 5-aminolevulinic acid, etc., is 50 μg to 50 mg, desirably 500 μg to 25 mg, more desirably 5 mg to 25 mg, in iron equivalent under the same conditions.

As an administration form of the hair restorer of the present invention, the following method is preferably exemplified but not limited thereto: the hair restorer of the present invention is transdermally administered from the twilight to the night by methods such as application, and is rinsed off on the same night.

One characteristic of the hair restorer and the method for restoring hair of the present invention resides in the point that there is no need for a strict light shielding treatment, which is necessary in case of single administration (application, etc.) of 5-aminolevulinic acid. However, it is preferable to avoid being exposed to strong light, for example, being in a scorching sun. The administration method of the present invention is conducted for 3 months as 1 course, and in many cases, hair restoring effects such as the reduction of hair loss and the appearance of new hair are seen from day 3. Though it could be used continuously, in case where the effect reaches a plateau, the effect can be expected again by stopping the administration once and resuming the administration 3 months later.

The present invention will be described more specifically with reference to Examples, but the technical scope of the present invention is not limited to these exemplifications.

EXAMPLE 1

Figure 1:
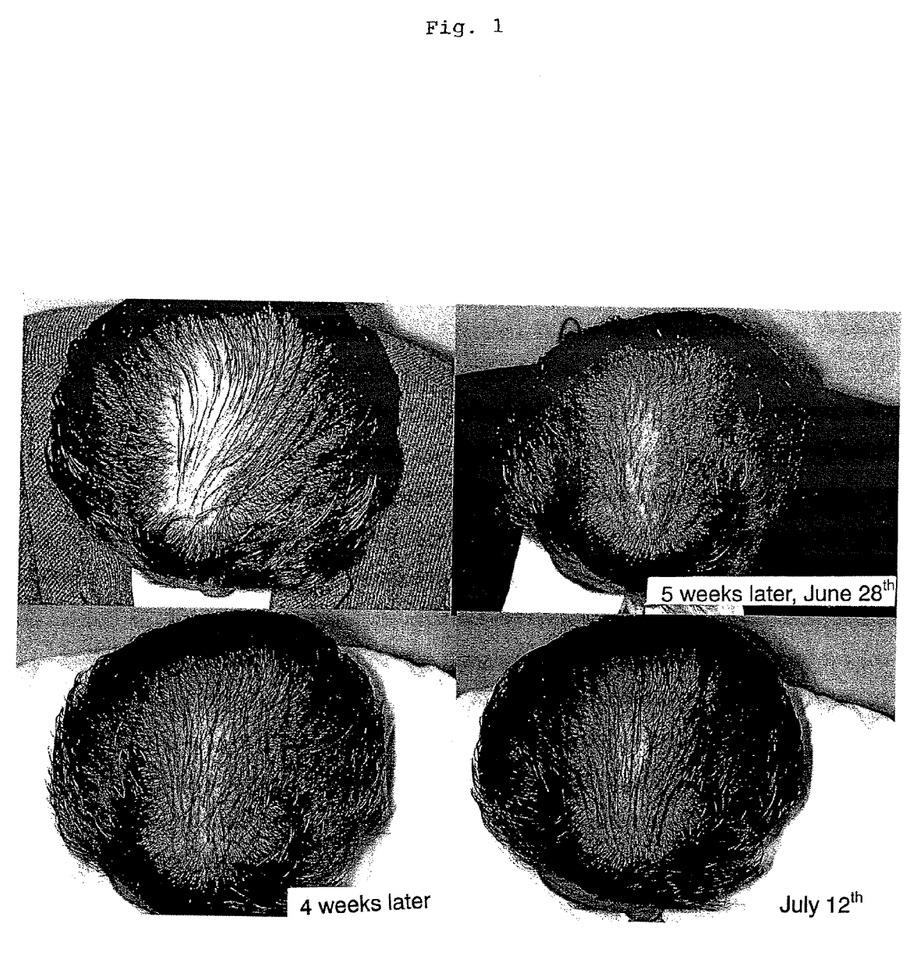
FIG. 1 is a set of photographs showing an example of clinical testing of the hair restorer of the present invention. The photographs on top left, bottom left, top right and bottom right were taken at the start of application, 4 weeks later, 5 weeks later and 7 weeks later (on July 12$^{th}$), respectively.

Into 20 ml of purified water wherein 4% of 1,3-butylene glycol and 0.15% of methylparaben were dissolved, 1.5 g of 5-aminolevulinic acid hydrochloride, 3 g of urea and 1 g of ferrous citrate were mixed well. This mixture, 3 ml in total, was applied every night to the top of the head of a human having hair thinning and bald spots. After the application, the head was left for 2 hours, and the mixture was rinsed off and the hair was washed on the same night. The conventional strict light shielding conditions applied when 5-aminolevulinic acids are used alone were not performed, and hair removal occurring when the dosage is partially excessive was not observed. The amount of loose hair attached to the pillowcase was observed to reduce 3 days after the start of the application. Two weeks later, outgrowth of fuzzy hair began to be noticeable. Photographs were taken at the start of application, 4 weeks later, 5 weeks later (June $28^{th}$), and 7 weeks later (July $12^{th}$). The set of photographs thus taken is shown in FIG. 1 (photographs). As shown in FIG. 1, 7 weeks later, outgrowth of terminal hair was clearly observed in comparison to the start of the application, and visually obvious increased hair was observed.

EXAMPLE 2

A hair restorer was prepared in a same manner as in Example 1, except that the amount of 5-aminolevulinic acid hydrochloride in Example 1 was changed to be 3 g, and an effect substantially equal to Example 1 was obtained.

EXAMPLE 3

A hair restorer was prepared in a same manner as in Example 1, except that the amount of ferrous citrate in Example 1 was changed to be 2 g, and an effect substantially equal to Example 1 was obtained.

EXAMPLE 4

A hair restorer was prepared in a same manner as in Example 1, except that 1 g of ferrous citrate in Example 1 was changed to be 4 g of iron ammonium diethylenetriaminepentaacetate, and an effect substantially equal to or stronger than Example 1 was obtained.

EXAMPLE 5

A hair restorer was prepared in a same manner as in Example 1, except that urea in Example 1 was not blended into, and an effect substantially equal to Example 1, except that the hair growth effect was slightly lowered, was obtained.

EXAMPLE 6

Figure 2:
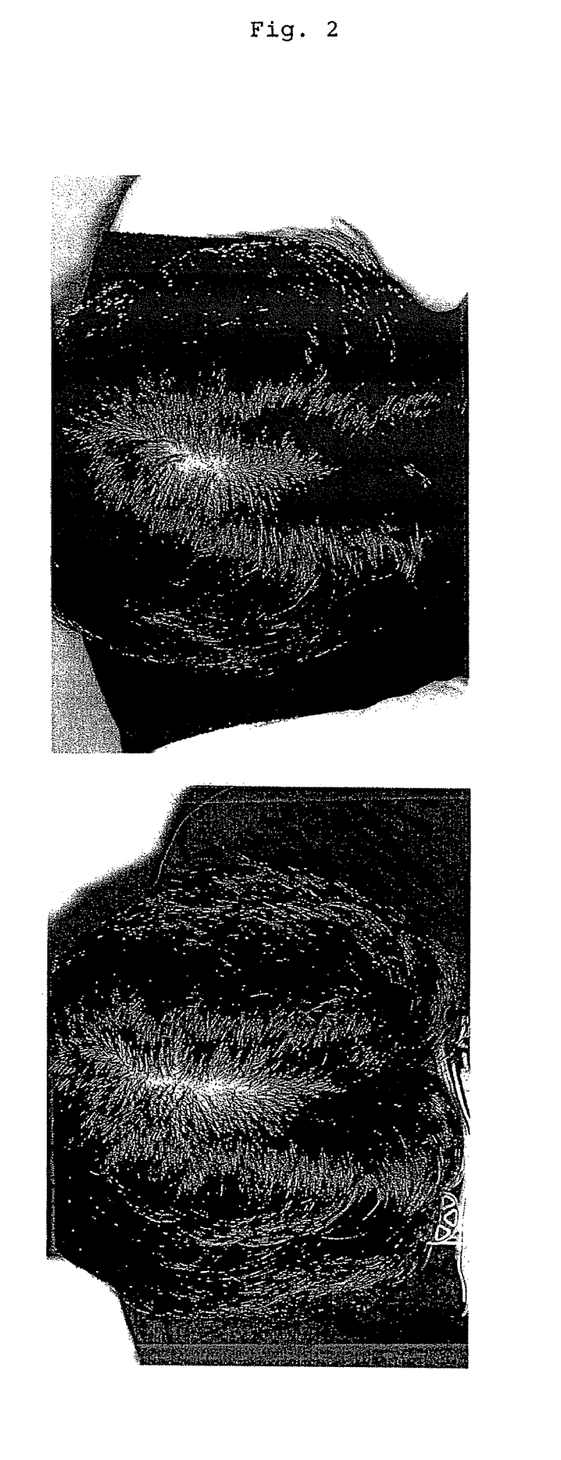
FIG. 2 is a set of photographs showing an example of clinical testing of the hair restorer of the present invention. The left and right photographs were taken at the start of application and 4 weeks later, respectively.

45 parts by weight of ethyl alcohol, 2 parts by weight of 5-aminolevulinic acid hydrochloride, and 5.6 parts by weight of iron ammonium diethylenetriaminepentaacetate were mixed and dissolved, and 0.7 part by weight of carboxy vinyl polymer was dispersed in this mixture, and subsequently 46.6 parts by weight of purified water was added for dissolution. To this solution, 0.7 part by weight of diisopropanaolamine was added, and the resultant mixture was stirred and mixed to prepare a gel-type hair restorer. With regard to this hair restorer, the conventional strict light shielding conditions applied when 5-aminolevulinic acids are used alone were not performed, and hair removal occurring when the dosage is partially excessive was not observed. The amount of loose hair attached to the pillowcase was observed to reduce 3 days after the start of the application. Two weeks later, outgrowth of fuzzy hair began to be noticeable. Photographs were taken at the start of application and 4 weeks later. The set of photographs thus taken is shown in FIG. 2 (photographs). As shown in FIG. 2, 4 weeks later, outgrowth of terminal hair was clearly observed in comparison to the start of the application, and visually obvious increased hair was observed.

EXAMPLE 7

A gel-type hair restorer was prepared in a same manner as in Example 6, except that 5-aminolevulinic acid hydrochloride in Example 6 was changed to be 5-aminolevulinic acid methyl ester, and an effect comparable to Example 6 was obtained.

EXAMPLE 8

Figure 3:
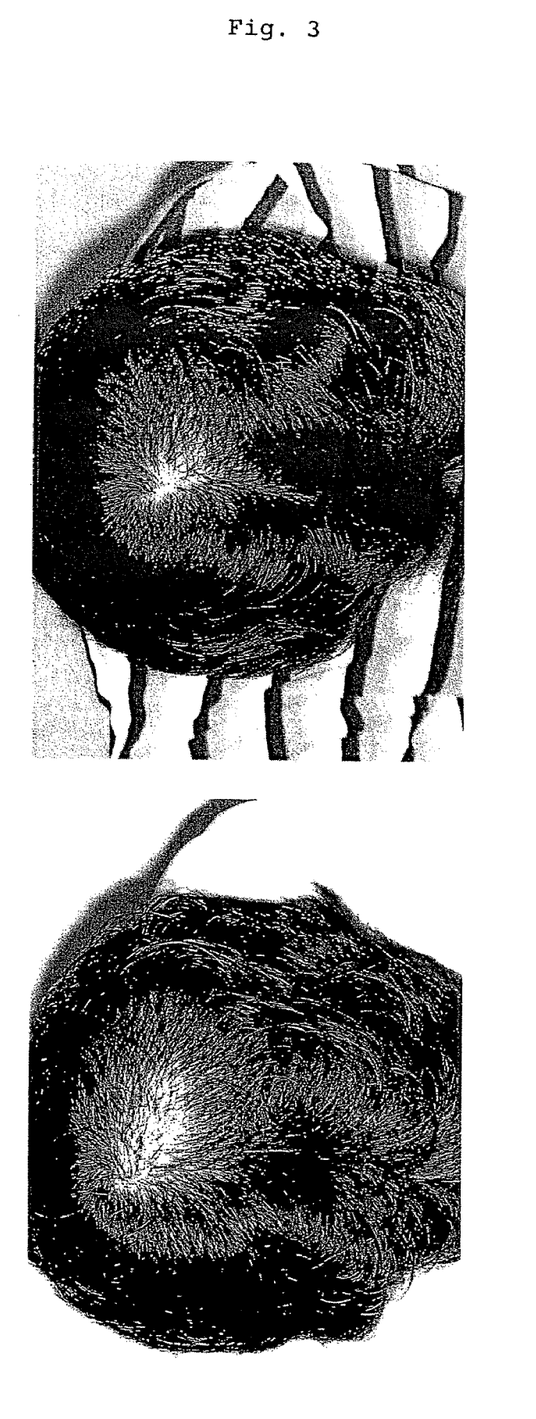
FIG. 3 is a set of photographs showing an example of clinical testing of the hair restorer of the present invention. The left and right photographs were taken at the start of application and 4 weeks later, respectively.

A gel-type hair restorer was prepared in a same manner as in Example 6, except that iron ammonium diethylenetriaminepentaacetate in Example 6 was changed to be iron sodium diethylenetriaminepentaacetate, and an effect substantially equal to or stronger than Example 6 was obtained. With regard to this hair restorer, the conventional strict light shielding conditions applied when 5-aminolevulinic acids are used alone were not performed, and hair removal occurring when the dosage is partially excessive was not observed. The amount of loose hair attached to the pillowcase was observed to reduce 3 days after the start of the application. Two weeks later, outgrowth of fuzzy hair began to be noticeable. Photographs were taken at the start of application and 4 weeks later. The set of photographs thus taken is shown in FIG. 3 (photographs). As shown in FIG. 3, 4 weeks later, outgrowth of terminal hair was clearly observed in comparison to the start of the application, and visually obvious increased hair was observed.

EXAMPLE 9

A gel-type hair restorer was prepared in a same manner as in Example 6, except that 5-aminolevulinic acid hydrochloride in Example 6 was changed to be 5-aminolevulinic acid phenethyl ester, and an effect comparable to Example 6 was obtained.

EXAMPLE 10

5 parts by weight of glyceryl monostearate, 2 parts by weight of isopropyl myristate, 5 parts by weight of liquid paraffin, 4 parts by weight of polyoxyethylene (20) sorbitan monostearate, 4 parts by weight of propylene glycol monoisostearate, 2 parts by weight of cetyl alcohol, 2 parts by weight of stearyl alcohol, 0.2 part by weight of vitamin E acetate, 0.1 part by weight of hinokitiol, 0.2 part by weight of glycyrrhetinic acid, and 5 parts by weight of iron lactate were stirred and dissolved while heated. Separately, 2 parts by weight of 5-aminolevulinic acid, 7 parts by weight of propylene glycol, 0.1 part by weight of parahydroxybenzoate ethyl and purified water in an amount to make the mixture 100 parts by weight in total were added, and stirred and dissolved while heated. This liquid was added to the above-mentioned solution, and the resultant mixture was stirred and mixed to prepare a cream-type hair restorer. With regard to this hair restorer, the conventional strict light shielding conditions applied when 5-aminolevulinic acids are used alone were not performed, and hair removal occurring when the dosage is partially excessive was not observed. In addition, the hair restoring effect was equal to or stronger than the case where 5-aminolevulinic acids were used alone.

EXAMPLE 11

A cream-type hair restorer was prepared in a same manner as in Example 10, except that 5 parts by weight of iron lactate in Example 10 was changed to be 1 part by weight of ferrous gluconate, and an effect comparable to Example 10 was obtained.

EXAMPLE 12

1 part by weight of 5-aminolevulinic acid methyl ester, 5 parts by weight of ferrous succinate, 0.0008 part by weight of β-estradiol, 0.2 part by weight of hinokitiol, 0.2 part by weight of glycyrrhetinic acid, 0.1 part by weight of vitamin E acetate, 55 parts by weight of ethyl alcohol, 4005 parts by weight of polyethylene glycol, 5 parts by weight of glyceryl monoisostearate and 0.3 part by weight of 1-menthol were stirred and dissolved. 4 parts by weight of polyoxyethylene (20) polyoxypropylene (6) decyltetradecyl ether, and 24.7 parts by weight of purified water were stirred and dissolved in advance. This liquid was added to the above-mentioned solution, and the resultant mixture was stirred and mixed to prepare a lotion-type hair restorer. With regard to this hair restorer, the conventional strict light shielding conditions applied when 5-aminolevulinic acids are used alone were not performed, and hair removal occurring when the dosage is partially excessive was not observed. In addition, the hair restoring effect was equal to or stronger than the case where 5-aminolevulinic acids were used alone.

EXAMPLE 13

3 parts by weight of polyoxyethylene (20) sorbitan monooleate, 5 parts by weight of propylene glycol, 15 parts by weight of ethyl alcohol, 1 part by weight of 5-aminolevulinic acid, iron sodium ethylenediaminetetraacetate, and purified water in an amount to make the mixture 100 parts by weight in total were mixed, and stirred and dissolved. This mixture was put into an aerosol can, and 4 parts by weight of liquefied petroleum gas was pressed and filled into the can to prepare an aerosol-type hair restorer. With regard to this hair restorer, the conventional strict light shielding conditions applied when 5-aminolevulinic acids are used alone were not performed, and hair removal occurring when the dosage is partially excessive was not observed. In addition, the hair restoring effect was equal to or stronger than the case where 5-aminolevulinic acids were used alone.

EXAMPLE 14

An aerosol-type hair restorer was prepared in a same manner as in Example 13, except that 1 part by weight of 5-aminolevulinic acid in Example 13 was changed to be 1 part by weight of 5-aminolevulinic acid methyl ester, the effect comparable to Example 13 was obtained.

EXAMPLE 15

To 70 parts by weight of ethyl alcohol, 5 parts by weight of propylene glycol, 0.5 part by weight of 5-aminolevulinic acid, 2 parts by weight of iron triethylenetetraamine, and purified water in an amount to make the mixture 100 parts by weight in total were added, and the resultant mixture was stirred and dissolved to prepare a lotion-type hair restorer. With regard to this hair restorer, the conventional strict light shielding conditions applied when 5-aminolevulinic acids are used alone were not performed, and hair removal occurring when the dosage is partially excessive was not observed. In addition, the hair restoring effect was equal to or stronger than the case where 5-aminolevulinic acids were used alone.

EXAMPLE 16

45 parts by weight of ethyl alcohol, 1 part by weight of 5-aminolevulinic acid, and 2 parts by weight of iron acetate, 5 parts by weight of 1,3-butandiol, and purified water in an amount to make the mixture 100 parts by weight in total were added, and the resultant mixture was stirred and dissolved, and 0.7 part by weight of carboxy vinyl polymer was dispersed in this mixture. To this solution, 0.7 part by weight of diisopropanaolamine was subsequently added, and the resultant mixture was stirred and mixed to prepare a gel-type hair restorer. With regard to this hair restorer, the conventional strict light shielding conditions applied when 5-aminolevulinic acids are used alone were not performed, and hair removal occurring when the dosage is partially excessive was not observed. In addition, the hair restoring effect was equal to or stronger than the case where 5-aminolevulinic acids were used alone.

EXAMPLE 17

A gel-type hair restorer was prepared in a same manner as in Example 16, except that iron oxalate was used instead of iron acetate in Example 16, and an effect comparable to Example 16 was obtained.

EXAMPLE 18

Hair Growth Test

In Table 1, 5-aminolevulinic acid (sometimes abbreviated as ALA) of the present invention and iron compounds, and the blend compositions of them and urea are shown in wt %. For 1 g of ALA, 0.4 g of ferrous citrate, 2.81 g of iron lactate, 5.7 g of iron sodium diethylenetriaminepentaacetate, 5.6 g of iron ammonium diethylenetriaminepentaacetate, and 0.36 g of ferrous gluconate were blended respectively. The body hair on the backs of C3H/HeNCrJ mice (n=3 in each group), which were in telogen phase of hair growth cycle, was clipped with a hair clipper, and each suspension shown in Table 1 was applied to the back once a day, in an amount of 0.2 ml, by spraying uniformly. Two weeks later, body hair on the back of each mouse was depilated, and the length of hair was measured under a microscope. The results are shown in Table 1.

TABLE 1

| Sample No. | Compositions ALA | Iron compound | Urea | Hair length after 2 weeks (mm) |
|---|---|---|---|---|
| 1 | 2% Solution | Ferrous citrate | 0% | 1.12 |
| 2 | " | " | 10% | 1.48 |
| 3 | " | Iron lactate | 0% | 1.00 |
| 4 | " | " | 10% | 1.20 |
| 5 | " | Iron sodium diethylenetriamine-pentaacetate | 0% | 1.82 |
| 6 | " | Iron sodium diethylenetriamine-pentaacetate | 10% | 2.96 |
| 7 | " | Iron ammonium diethylenetriamine-pentaacetate | 0% | 1.68 |
| 8 | " | Iron ammonium diethylenetriamine-pentaacetate | 10% | 2.14 |
| 9 | " | Ferrous gluconate | 0% | 1.48 |
| 10 | " | " | 10% | 1.46 |
| Control | " | Nil | 0% | 1.08 |
| Control | | 0.1% Croton oil | | 1.90 |
| Control | | 5% Minoxidil | | 1.70 |
| Control | | Distilled water | | 1.22 |

Figure 4:
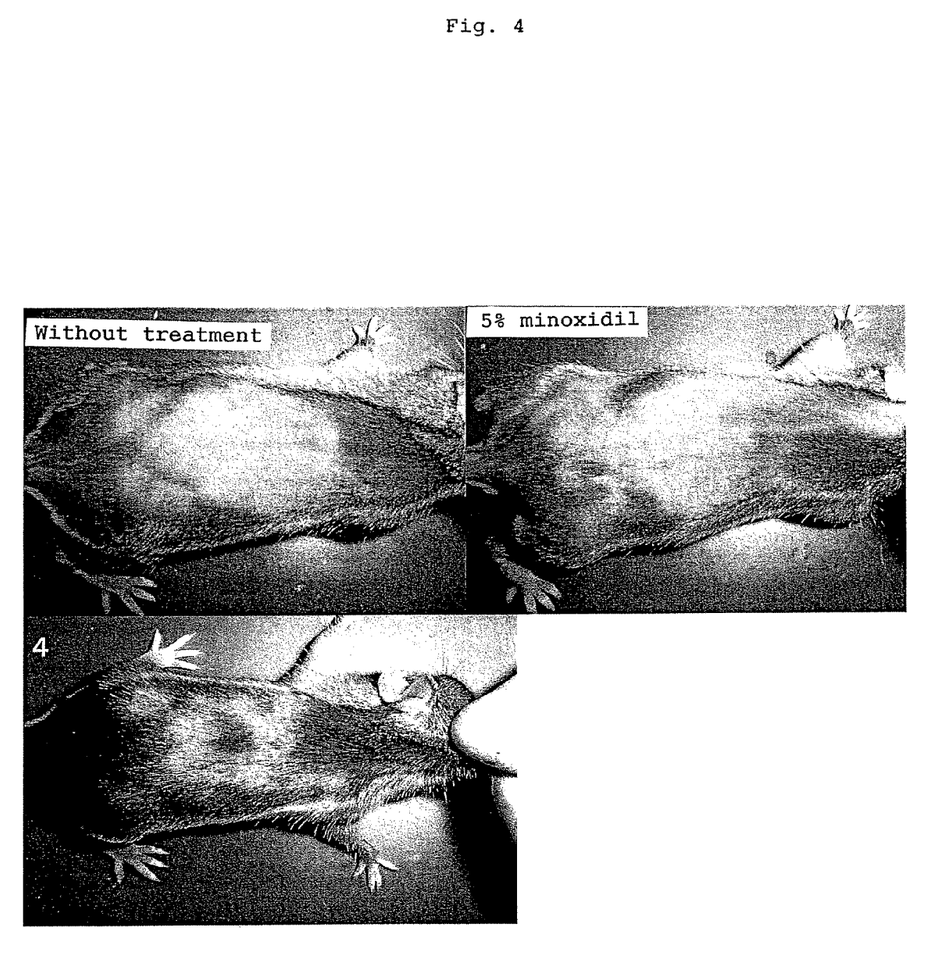
FIG. 4 is a set of photographs showing hair growth of mice 20 days after the application of the hair restoring composition of the present invention. The photographs on top left, top right and bottom left shows a mouse without treatment, a mouse applied with 5% minoxidil, and a mouse applied with the composition No. 14 of the present invention, respectively.

In addition, photographs of the backs of mice on which the sample No. 8 of the present invention, 5% minoxidil (positive control), and distilled water (negative control) were respectively applied were taken 20 days after the application. The results are shown in FIG. 4 (photographs). As shown in FIG. 4, there are remarkable differences in amount, length and shine of hair, between the hair of mice applied with the sample of the present invention and with distilled water (negative control), indicating that the sample is excellent in the hair restoring effect. Further, even in comparison to the case using minoxidil which is conventionally used, the sample of the present invention exhibited comparable effects in amount, length and shine of hair, indicating its excellence.

INDUSTRIAL APPLICABILITY

The present invention using 5-aminolevulinic acids and iron compound, in particular, iron sodium diethylenetriaminepentaacetate or iron ammonium diethylenetriaminepentaacetate in combination, makes it possible to provide a hair restorer which does not have problems such as hair loss, hair thinning, split ends, and hair graying, for which light shielding at the point of use is not an absolute requirement, whose usage is simple, and which exhibits a remarkable hair restoring effect equal to or stronger than the case where 5-aminolevulinic acids are used alone.

The invention claimed is:

1. A method for restoring hair comprising
administering transdermally a hair restorer that comprises one or more compounds selected from 5-aminolevulinic acid, 5-aminolevulinic acid salt thereof and 5-aminolevulinic acid ester wherein the ester having 1-24 carbon atoms, salt, and an iron compound wherein the iron compound is iron sodium diethylenetriaminepentaacetate or iron ammonium diethylenetriaminepentaacetate, as active components, wherein dosage of the one or more compounds is 10 μg to 10 mg in terms of 5-aminolevulinic acid hydrochloride equivalent and wherein dosage of the iron compound is 50 μg to 50 mg in terms of iron equivalent.

2. The method for restoring hair according to claim 1, wherein a hair restorer further comprises urea as an active component.

* * * * *

UNITED STATES PATENT AND TRADEMARK OFFICE
CERTIFICATE OF CORRECTION

PATENT NO. : 8,133,479 B2
APPLICATION NO. : 11/568322
DATED : March 13, 2012
INVENTOR(S) : Yoshiyasu Ito Page 1 of 1

It is certified that error appears in the above-identified patent and that said Letters Patent is hereby corrected as shown below:

In Claim 1, line 6 (Col. 11, line 10) delete "salt,"

Signed and Sealed this
Twelfth Day of June, 2012

David J. Kappos
*Director of the United States Patent and Trademark Office*